(12) United States Patent
Larré

(10) Patent No.: US 6,210,433 B1
(45) Date of Patent: Apr. 3, 2001

(54) STENT FOR TREATMENT OF LESIONS OF BIFURCATED VESSELS

(76) Inventor: Jorge Casado Larré, Ave Los Próceres Urbanización Las Flores Merida, Merida (VE)

( * ) Notice: Subject to any disclaimer, the term of this patent is extended or adjusted under 35 U.S.C. 154(b) by 0 days.

(21) Appl. No.: 09/527,355

(22) Filed: Mar. 17, 2000

(51) Int. Cl.[7] .................................................. A61F 2/06
(52) U.S. Cl. ................................. 623/1.15; 623/1.35
(58) Field of Search .................................. 606/191, 194, 606/198, 195; 623/1.1, 1.15, 1.35, 1.12, 1.16, 1.2

(56) References Cited

U.S. PATENT DOCUMENTS

| | | | |
|---|---|---|---|
| 4,994,071 | 2/1991 | MacGregor | 606/194 |
| 5,575,816 | * 11/1996 | Rudnick et al. | 623/1.15 |
| 5,591,230 | * 1/1997 | Horn et al. | 623/1.17 |
| 5,632,771 | * 5/1997 | Boatman et al. | 623/1.15 |
| 5,643,312 | * 7/1997 | Fischell et al. | 623/1.15 |
| 5,676,697 | * 10/1997 | McDonald | 623/1.35 |
| 5,931,866 | * 8/1999 | Frantzen | 623/1.15 |
| 6,001,125 | * 12/1999 | Golds et al. | 623/1.15 |

\* cited by examiner

*Primary Examiner*—Michael H. Thaler
*Assistant Examiner*—Kristen Droesch
(74) *Attorney, Agent, or Firm*—J. Sanchelima

(57) ABSTRACT

A stent to be used in angioplastic procedures including a parabolically extending support member; and several hyperbolic transverse members. The parabolically extending support member includes several through openings through which the hyperbolic transversed members are mounted. In the contracted state, the main branch and both secondary branches extend parallel to each other. When expanded, the stent defines two secondary branches and one main branch. The junction of the two secondary branches are protected in the same fashion as a pair of pants or a horse saddle.

2 Claims, 2 Drawing Sheets

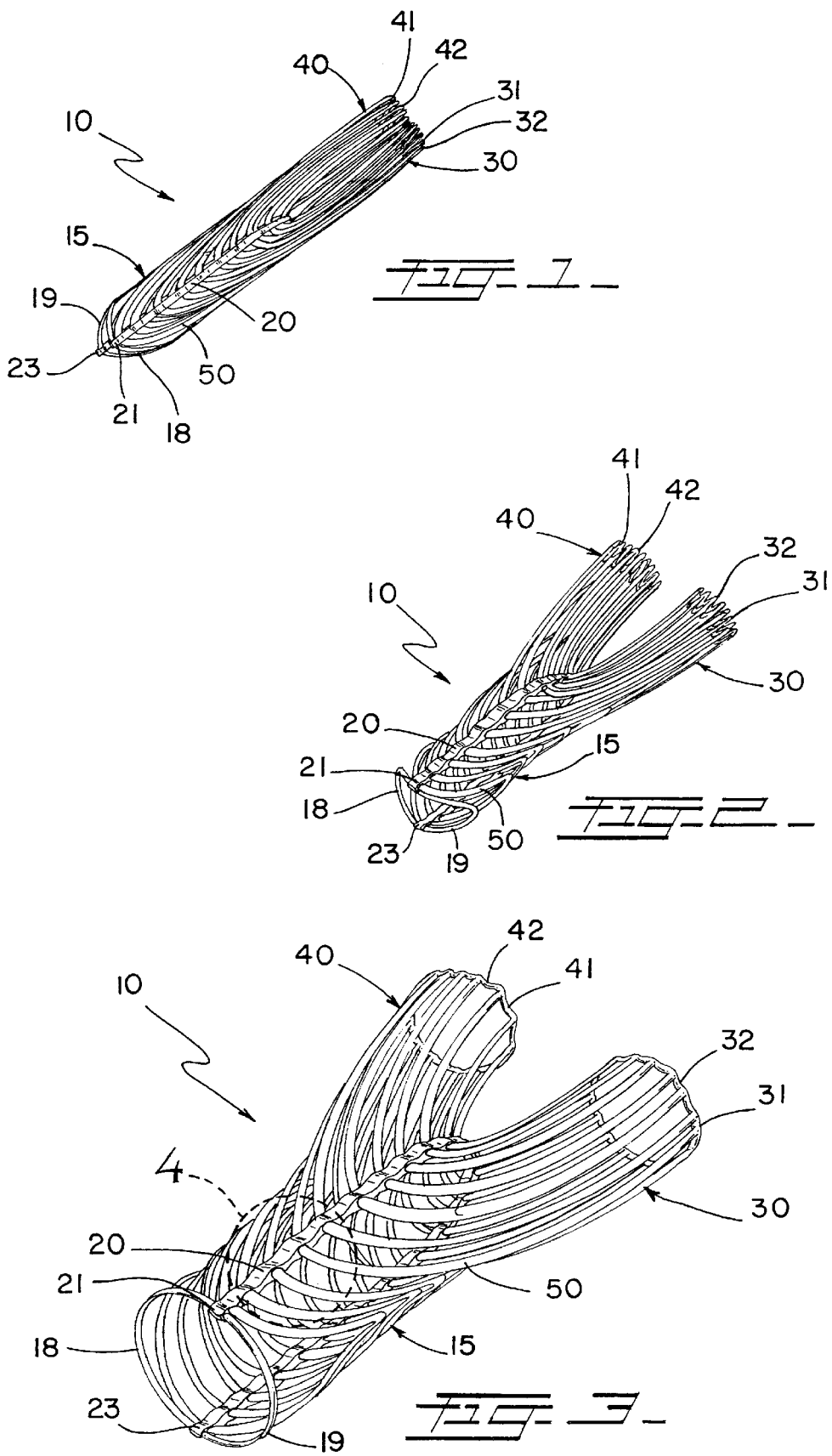

STENT FOR TREATMENT OF LESIONS OF BIFURCATED VESSELS

BACKGROUND OF THE INVENTION

1. Field of the Invention

The present invention relates to devices that are used in angioplastic procedures, and more particularly, to those known as stents used when the lesions being treated are on or near bifurcated vessels.

2. Description of the Related Art

The treatment of lesions in or in the neighborhood of a bifurcated vessel through angioplastic procedures requires special considerations for the affixation of devices called stents. After dilatation occurs using a balloon, athrectomy, or laser, a stent is utilized to correct an abrupt closure in the area being treated, and to assist in the process of treating restenosis patients. To correct lesions in bifurcated vessels and to place the prosthesis in place is difficult, of great risk to the patient, and labor intensive for the physician. At present there are no prosthesis that covers and protects the crotch junction of the bifurcated vessels and surrounding areas. The present invention addresses this problem.

The possibility of collapse or blocking one of the two branches of a bifurcated vessel is always present. Therefore, it is desirable to use a method for delivering stents that maintains a guiding member on each one of the two branches, permitting a physician to react promptly in case of emergency (i.e. vessel collapse). With respect to the stents that have been used in the past, the characteristics of these devices include predetermined malleability to cooperate with an inflatable balloon to attach a stent to the inner surface of the vessels. The stents that have been designed in the past are not protective enough of the junction point for the two branches of a bifurcated vessel. One of these examples is U.S. Pat. No. 4,994,071 issued to MacGregor in 1991 for Bifurcating Stent Apparatus and Method wherein several substantially circular members are used to define the stent for bifurcated vessels. It can be seen that the junction point of the bifurcated vessel is left without protection.

The present invention provides for the cooperative and interconnected disposition of hyperbolic elements along a parabolic path that permit the contraction of the elements which can be readily expanded through an inflatable balloon such as those used in angioplastic procedures. This volumetrically efficient device effectively protects the junction area of bifurcated vessels. It resembles a horse saddle in its configuration.

SUMMARY OF THE INVENTION

It is one of the main objects of the present invention to provide a stent for angioplastic use that is capable of providing maximum protection for the junction area defined by the two secondary branches of a bifurcated vessel and the areas abutting to the junction, such as the main and secondary branches.

It is another object of this invention to provide such a stent that can be readily expanded by the utilization of an angioplastic balloon thus facilitating its transportation to the area of the lesion.

It is still another object of the present invention to provide a stent that resembles a pair of pants in the crotch area that follows the contour of a typical saddle horse.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 is an isometric representation of the stent in contracted configuration.

FIG. 2 illustrates the stent shown in FIG. 1 in and expanded configuration.

FIG. 3 shows the stent of the previous two figures fully expanded.

DETAILED DESCRIPTION OF THE PREFERRED EMBODIMENT

Figure 4:
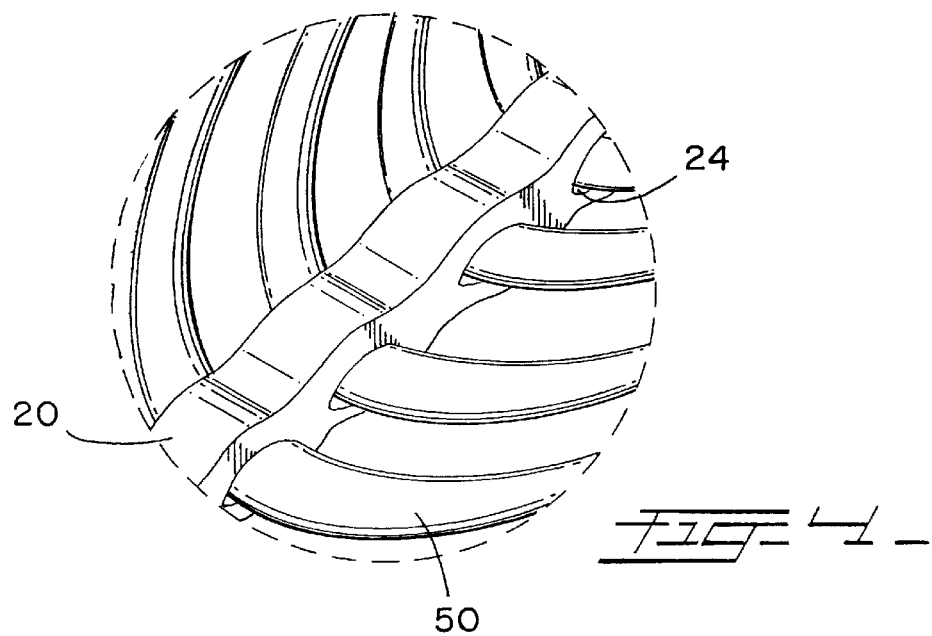
FIG. 4 is a detailed isometric view of the parabolic structural support member with several hyperbolic transverse members partially shown, taken from FIG. 3.
Figure 5:
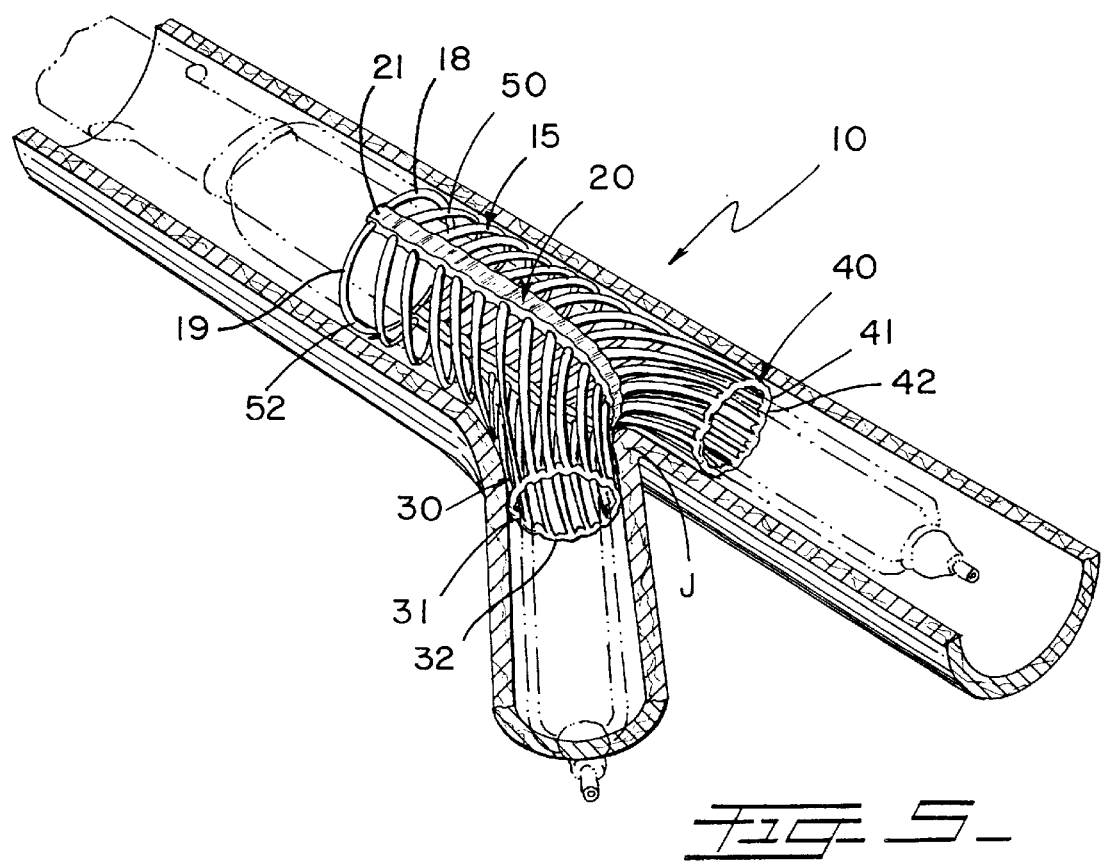
FIG. 5 shows the stent subject of the present invention mounted over an inflated balloon and fully expanded.

Referring now to the drawings, where the present invention is generally referred to with numeral 10, it can be observed that in its contracted shape it is substantially a cylindrical member and, as it expands, adopts the shape of a pair of pants. This is shown in FIGS. 1 through 3.

To provide protection to the junction J of the two branches of a bifurcated vessel, the present invention provides a parabolic structural member 20 having ends 21 and 23. Member 20 extends longitudinally from end 21 passing through junctions J and returns to end 23 opposite to end 21. Ends 21 and 23 are connected to flexible ring 18 defining the end 19 of main branch 15. Several transverse hyperbolic members 50 are transversely disposed with respect to parabolic member 20 and runs from one end 31 of branch 30 to the other end 41 of branch 40 passing through opening 24 of parabolic member 20. Hyperbolic members 50 extend towards branches 30 and 40, radially therealong, defining the surfaces of branches 30 and 40.

In the preferred embodiment, the applicant contemplates having a separation of less than one millimeter between transverse hyperbolic members 50. To produce stents, a variety of materials can be used, either alone or in combination, such as metals or alloys (stainless steel, titanium, tantalum, nitinol, Elgiloy, NP35N) that can vary in their springiness, malleability, and response to temperature; polymers (poly-urethane, polyether sulfone, polyimide, polycarbonate, polyethylene, etc.) that can vary in their ability to bioabsorb or biodegrade; carbon; and ceramics. Various surface treatments can be applied to render the stents more biocompatible (pyrolytic carbon, hydrogels, etc.) and to provide for the elution of drugs (heparin, antiplatelet agents, platelet-derived growth factor, antibiotics, steroids, etc.). The physical characteristics of this material are compatible with the affixation of these stents to the inner walls of the vessels treated.

Parabolic structural member 20 includes a predetermined number of through openings 24 through which transverse hyperbolic members 50 pass and are rotatably journalled thereon. In the collapsed configuration the ends of members 50 abuttingly extend substantially parallel with respect to each other defining branches 30 and 40. The ends 31 and 41 are defined with ring members 32 and 42 to which the ends of member 50 are attached. Ring members 32 and 42 have a substantially zig-zag shape that is deformed to get an substantially flattened shape when the stent is positioned and fully expanded, as best seen in FIGS. 1 through 3. The malleability of the material used on ring members 32 and 42 permits them to keep their form once expanded and placed against the interior walls of the vessels being treated. Ring members 32 and 42 are made of stainless steel, combinations or alloys such as used in Bard XT Carina Bifurcated Stent manufactured by Bard, Inc., Billerica, Mass.

In the expanded configuration, the ends of members 50 are kept at a spaced apart and parallel relationship with respect to each other defining branches 30 and 40 with a lumen therein of predetermined dimensions.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A stent to be used in angioplastic procedures for the treatment of lesions in or about the bifurcated areas of vessels, comprising:

A) a parabolically extending support member having a plurality of transverse through openings at predetermined distances from each other and further including first and second ends;

B) a plurality of hyperbolically extending transverse members rotatably mounted to said through openings and further including third and fourth ends and a central portion in between so that, in the collapsed configuration, said first and second ends extend substantially parallel to each other with a relatively small separation in between and said third ends are kept at a parallel and abutting relationship with respect to each other thereby defining a first substantially cylindrical secondary branch and said fourth ends being kept at a parallel and abutting relationship with respect to each other defining a second substantially cylindrical secondary branch and, in the expanded configuration, said first and said second ends being separated from each other a predetermined distance with the central portions of said plurality of hyperbolically extending transverse members defining a main branch.

2. The stent set forth in claim 1 further including:

C) two ring members, one for said first substantially cylindrical secondary branch and one for said second substantially cylindrical secondary branch, said ring members being mounted to said third and fourth ends respectively, thereby defining the terminations of said secondary branches.

* * * * *